United States Patent
Tolvanen-Laakso et al.

(10) Patent No.: US 7,130,673 B2
(45) Date of Patent: Oct. 31, 2006

(54) METHOD OF POSITIONING ELECTRODES FOR CENTRAL NERVOUS SYSTEM MONITORING AND SENSING PAIN REACTIONS OF A PATIENT

(75) Inventors: Heli Tolvanen-Laakso, Helsinki (FI); Hanna Viertiö-Oja, Espoo (FI); Markku Paloheimo, Espoo (FI)

(73) Assignee: Instrumentarium Corp. (FI)

( * ) Notice: Subject to any disclaimer, the term of this patent is extended or adjusted under 35 U.S.C. 154(b) by 389 days.

(21) Appl. No.: 10/409,679

(22) Filed: Apr. 8, 2003

(65) Prior Publication Data

US 2004/0204656 A1   Oct. 14, 2004

(51) Int. Cl.
*A61B 5/0478* (2006.01)
*A61B 5/0492* (2006.01)

(52) U.S. Cl. ............... 600/383; 600/393; 600/544; 600/546

(58) Field of Classification Search ............ 600/383, 600/393, 544, 546
See application file for complete search history.

(56) References Cited

U.S. PATENT DOCUMENTS

| | | | |
|---|---|---|---|
| 4,359,724 A | * | 11/1982 | Zimmerman et al. ........ 600/383 |
| 4,595,013 A | | 6/1986 | Jones et al. |
| 6,032,064 A | | 2/2000 | Devlin et al. |
| 6,272,378 B1 | | 8/2001 | Baumgart-Schmitt |
| 6,394,953 B1 | | 5/2002 | Devlin et al. |
| 6,934,570 B1 | * | 8/2005 | Kiani et al. ............... 600/372 |
| 2001/0031916 A1 | | 10/2001 | Bennett et al. |
| 2002/0019588 A1 | * | 2/2002 | Marro et al. ............... 600/383 |
| 2002/0177767 A1 | | 11/2002 | Burton et al. |
| 2002/0183605 A1 | | 12/2002 | Devlin et al. |
| 2003/0009096 A1 | | 1/2003 | Lahteenmaki |

* cited by examiner

*Primary Examiner*—Lee S. Cohen
(74) *Attorney, Agent, or Firm*—Andrus, Sceales, Starke & Sewall, LLP

(57) ABSTRACT

A method concerning measurements by using an electrode array comprising three electrodes for central nervous system (CNS) monitoring from the forehead of a patient's head. A first electrode of said three electrodes is positioned between the eyebrows or immediately above the eyebrows of the patient. A third electrode of said three electrodes is positioned apart from the first electrode on the hairless frontolateral area of the forehead the patient. A second electrode is positioned between the first and the third electrodes on the forehead of the patient.

17 Claims, 5 Drawing Sheets

METHOD OF POSITIONING ELECTRODES FOR CENTRAL NERVOUS SYSTEM MONITORING AND SENSING PAIN REACTIONS OF A PATIENT

BACKGROUND OF THE INVENTION

The present invention relates to a method for central nervous system (CNS) monitoring, and more specifically to a method of positioning electrodes in an electrode array comprising three electrodes for monitoring central nervous system (CNS), ie electroencephalography (EEG) and frontal electromyography (FEMG) signals from the forehead of a patient's head. The invention also relates to a method of sensing pain reactions of a patient.

Electroencephalography (EEG) is a well-established method for assessing the brain function by picking up the weak signals generated in the brain with electrodes on the skull surface. To obtain the signals, multiple electrodes are placed on the scalp of a patient in accordance with a recognized protocol. EEG has been in wide use for decades in basic research of the neural system of brain as well as clinically in diagnosis of various neurophysiological disorders.

In a traditional EEG measurement electrodes are attached following the standard 10–20 system. Said system has been used by neurophysiologists for decades to record EEG and to find pathological EEG changes. The system however requires cumbersome attachment of multiple electrodes, especially, when the electrodes are attached in the hair environment.

One of the special applications for EEG which has received attention to during the 1990's is use of a processed EEG signal for objective quantification of the amount of brain activity for the purpose of determining the level of consciousness of a patient. In its simplest form, the usage of EEG allows for the automatic detection of the alertness of an individual, ie. if he or she is awake or asleep. This has become a significant issue, both scientifically and commercially, in the context of measuring the depth of unconsciousness induced by anesthesia during surgery. Modern anesthesia practices use a sophisticated balanced anesthesia technique with a combination of drugs for maintaining adequate hypnosis, analgesia, muscle relaxation, and suppression of the autonomic nervous system. The need for a reliable system for monitoring of the adequacy of the anesthesia is based on both safety and economical concerns. An anesthesia dose which is too light can, in the worst case, cause the patient wake up in the middle of the operation and create a highly traumatic experience both for the patient and for the personnel administering the anesthesia. At the opposite extreme, the administration of too much anesthesia generates increased costs due to the excessive use of anesthesia drugs and the time needed to administer the drugs. Over dosage of the anesthesia drugs also affects the quality and length of the post-operative period immediately after the operation and the time required for any long-term post-operative care.

In the anesthesia and the intensive care environment said 10–20 system is very rarely used. This is because these environments are already crowded by many other measuring systems, such as blood pressure, ECG, inspired and expired gas measurements. The additional labour-consuming measuring system would take too much time and effort from the care personnel. There is even though need for central nervous system monitoring in these areas. The consciousness level of the patient is varied in both of said environments and till today there has not been a practical method for monitoring the level of consciousness in the anesthesia and the intensive care environment.

As told before in the anesthesia environment patient is anesthetized with hypnotic, analgesic and neuromuscular blocking agents. The neuromuscular blocking agents, given in a certain extent block the neuromuscular junction and the patient looses ability to move herself/himself. This can create a situation where patient feels pain but cannot communicate. Without central nervous system monitoring there is a risk of giving too little or too much anesthetics. If too little hypnotic drugs is given to the patient she/he could awake during operation, which could cause traumatic experience especially for the patient and also for the personnel. On the other hand over dosage of hypnotic drugs affects the quality and length of the post-operative period.

The above mentioned reasons have generated commercial efforts to develop EEG devices to said environments during the past ten years. The main requirements for such monitoring can be described by the following features, ease of use, reliability and good quality. The efforts in this area have concentrated into reliable and easy electrodes as well as to good quality signal processing.

A significant advancement in making the EEG-based measurement of the adequacy of anesthesia an easy-to-use, routine was a finding based on Positron Emission Tomography (PET) that determined that the effects of the anesthetic drugs on the brain are global in nature. This means that for many applications it is enough to measure the forebrain or frontal cortex EEG from the forehead of the patient. The forehead is both an easy to access and is hairless location on the patient. Electrodes placed with an appropriate spacing between the electrodes on the forehead can pick up an adequate signal originating from the anterior cortex in the brain.

Since the Positron Emission Tomography (PET) studies have shown that the anesthesia effect is a global phenomena in the brain, the sensor development efforts have concentrated on the hairless frontal area of the head. The first commercial sensor for this application area was developed by the company Aspect Medical Systems, Inc. U.S. Pat. No. 6,032,064 can be mentioned as an example of the art describing the sensor developed by Aspect Medical Systems, Inc. The company mentioned above also has patented many electrode configurations relating to placement of the electrodes on frontal and temple areas of the patient's head. Reference is made here to U.S. Pat. No. 6,394,953.

While the foregoing has discussed the use of EEG signals, it is also desirable to obtain frontal electromyographic (FEMG) signals arising from the forehead of the patient. The frontalis muscle is the first indicator of approaching consciousness. When this muscle activity is sensed by appropriately placed electrodes it provides an early indication that the patient is emerging from anesthesia. Similarly these electrodes can sense pain reactions originating from this same muscle activity when the anesthesia is not adequate, for example because of inadequate analgesia. So the FEMG signals give an early warning of arousal and may also indicate inadequate analgesia.

SUMMARY OF THE INVENTION

The object of the invention is to provide a simple and practical method of positioning an electrode array so that the electrodes of the array are optimally located for recording EEG and FEMG signals.

An advantage of the invention is in that the method is extremely simple, practical and reliable, and therefore optimal measuring results can be obtained. Another advantage of the invention is in that the method can be materialized very simply, ie. by using a simple electrode array, whereby costs can be kept at reasonably low level.

BRIEF DESCRIPTION OF THE DRAWINGS

In the following the invention will be described in greater detail by means of the examples described in the attached drawing, in which.

DETAILED DESCRIPTION OF TITLE INVENTION

Figure 1:
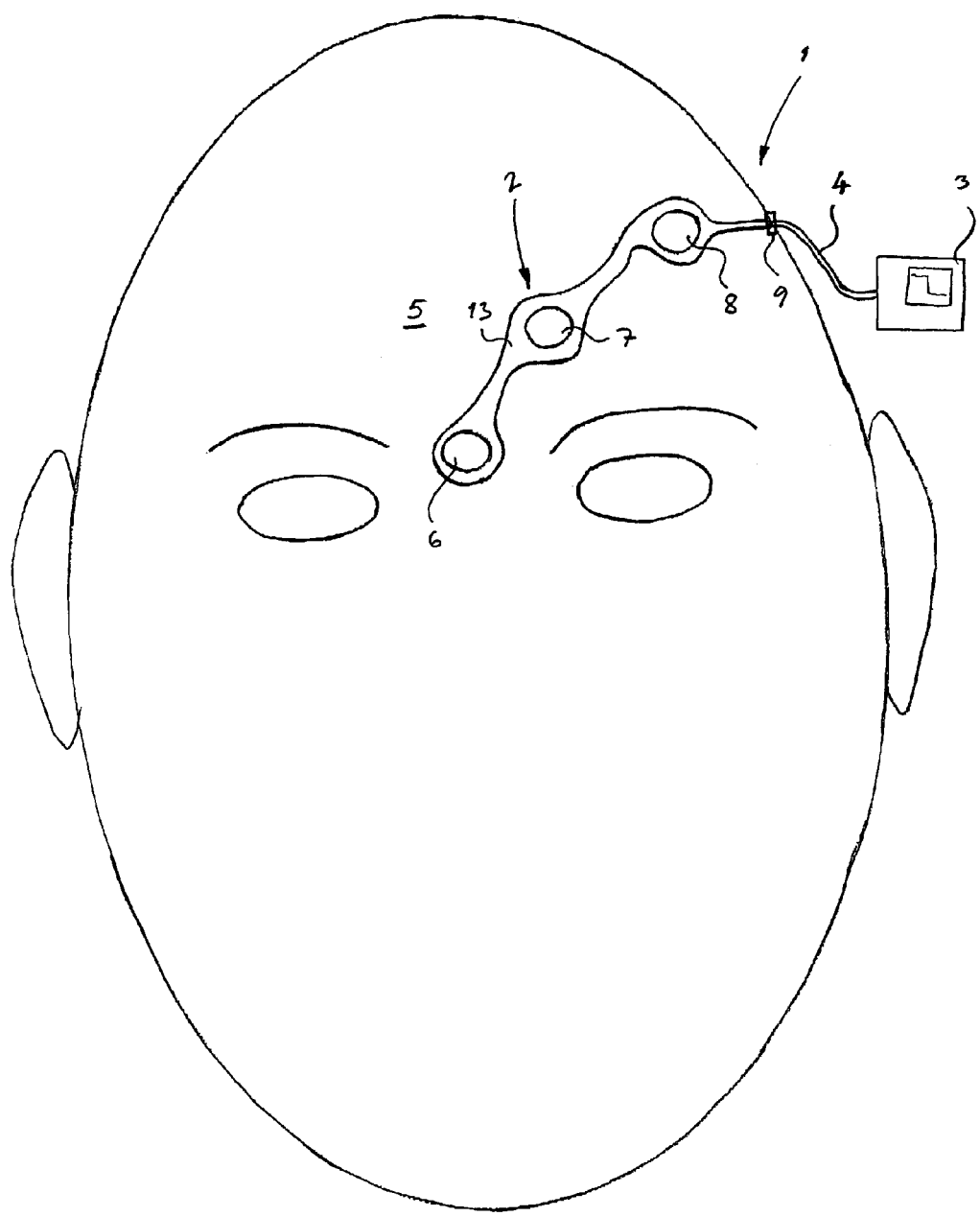
FIG. 1 shows a frontal view of a human head where electrodes are positioned according to the first embodiment of the invention.

Referring now to the figures in which corresponding details in different embodiments have been marked with same reference numerals, the sensor measurement system of the present invention is indicated generally at 1 in FIG. 1. The system 1 includes an electrode array 2 connected to a monitor 3 by a cable 4. The array 2 transmits central nervous system (CNS) signals from the forehead 5 of the patient to the monitor 3, which carries out signal processing and displays EEG and FEMG data in desired form. The data obtained can also be stored for future use.

Figure 5:
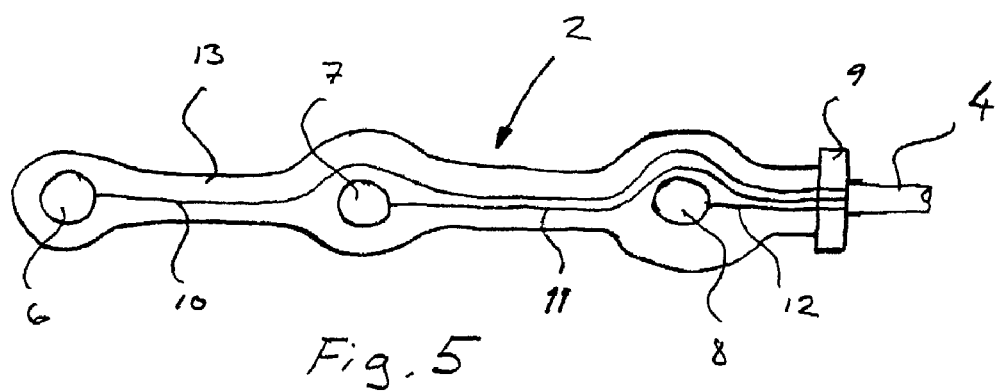

The electrode array 2 shown in FIG. 1 comprises three electrodes, ie. the first electrode 6, the second electrode 7 and the third electrode 8. The structure of the array 2 is shown more clearly in FIG. 5. The electrodes 6, 7 and 8 have been connected to a connector 9 by using conductors 10, 11 and 12. The electrodes and the conductors have been placed on a flexible substrate 13 made of an appropriate material, for example plastic material. The shape of the substrate can comprise three main bodies connected to each other by narrow extensions as shown in FIG. 5. Said form is advantageous because narrow extensions enable that positions of the electrodes when compared to each other can be varied according to the existing need when the array is placed on the forehead of the patient. It is however quite possible that the substrate is formed to be essentially of rectangular shape etc.

The first electrode 6 is used to measure phasic and tonic activation of facial muscles intended for expression of painful mimic responses (corrugator, procerus, frontalis and orbicularis oculi muscles), the FEMG signal. The first electrode 6 measures also some EEG related signal. The third electrode 8 measures cortical activity (EEG) of either frontal lobe from the hairless fronto-lateral area and only some FEMG related signal. The second electrode 7 is a ground electrode.

Figure 2:
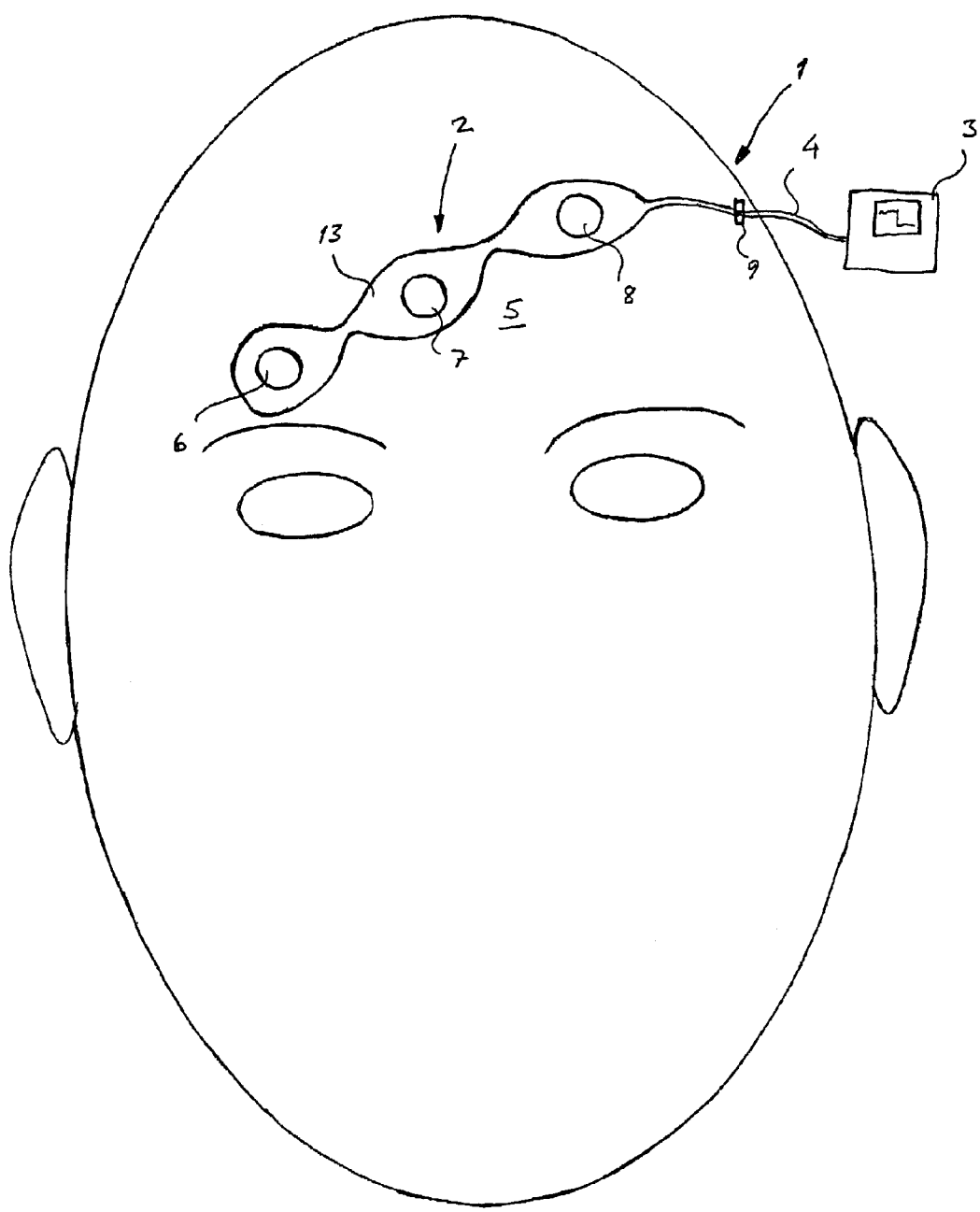
FIG. 2 shows a frontal view of a human head where electrodes are positioned according to the second embodiment of the invention.

According to the basic idea of the invention the first electrode 6 is positioned between the eyebrows of the patient as shown in FIG. 1 or immediately above either of the eyebrows, ie. above the eyebrows near frontalis and orbicularis muscles of the patient, as shown in FIG. 2. The third electrode 8 is positioned apart from the first electrode 6 on the hairless frontolateral area of the frontal lobe of the patient as shown in FIGS. 1 and 2. Preferably the third electrode 8 is positioned as far as possible from the first electrode 6. The second electrode 7 is positioned between the first electrode 6 and the third electrode 8 on the forehead of the patient as shown in FIGS. 1 and 2. It is very advantageous to place the second electrode 7 essentially in the middle of the first and the second electrodes so that the distances between the second electrode 7 and the first electrode 6, and the second electrode 7 and the third electrode 8 are essentially the same. This gives the opportunity to optimize Common Mode Rejection Ratio (CMRR) of the measured signal.

The three-electrode system described above and placed according to the basic idea of the present invention offers a simple solution to optimize both the EEG and FEMG signals at the same time. This is due to the fact that EEG and FEMG signals are best recorded when both measuring electrodes, ie. the first electrode 6 and the third electrode 8 are situated on the forehead of the patient. The first electrode 6 is placed on the area of the forehead in which the FEMG signal is stronger than the EEG signal. The third electrode 8 is placed on the area of the forehead in which the EEG signal is stronger than the FEMG signal. EEG signals of the hairless area of the forehead arise from the fronto-lateral area of the frontal lobe of the patient. FEMG signals arise from the forehead between the eyebrows or just above the eyebrows near frontalis and orbicularis muscles of the patient, ie. on the area where the facial muscles intended for expression of painful responses are situated. In other words one electrode collects a particularly high EMG-contribution from the muscle-rich region close to the eyebrows, while the voltage difference between the two electrodes over the fronto-lateral area measures a high EEG signal component. When measuring pain reactions the electrodes can be placed more freely than described above. For example the first electrode 6 would be placed as told above to enhance the FEMG signal. The other electrodes, the second one 7 and the third one 8 can be placed on the hairless areas of the head, for example frontal lobe, temples, cheeks, ears or areas around the ears. The third electrode 8 can be positioned apart from the first electrode 6 and the second electrode 7 can be positioned between the first and the second electrodes. Preferably however the second electrode 7 is placed in the middle of the first electrode 6 and the third electrode 8. In this connection it is important to realize that the embodiments shown in the Figures are suitable also for measuring pain reactions. As told above the FEMG signals give an early warning or indication of pain reactions of the patient, ie. according to the basic idea of the invention said signals can advantageously be used for better detecting emerging arousal and possible inadequate analgesia. When measuring pain reactions the EEG signal is not necessarily needed. When the EEG signal is not used the third electrode can act for example as a reference electrode. It is however advantageous to monitor also the EEG signal when pain reactions are measured.

The EEG and FEMG signals can be recorded with only three electrodes situated on the forehead of the patient. This simple three-electrode system situated according to the basic idea of the invention on the forehead offers a practical possibility to optimise both the EEG and FEMG signals at the same time.

Figure 3:
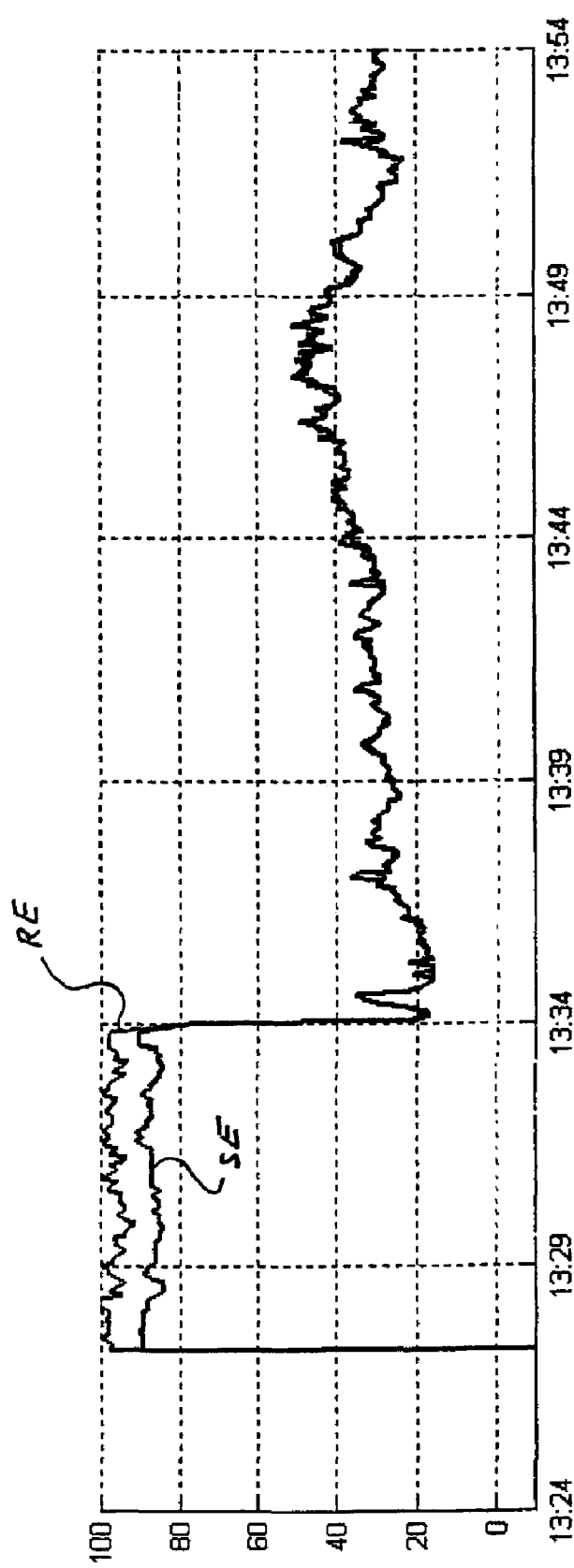
FIG. 3 is a diagram showing State Entropy (SE) and Response entropy (RE) when the patient is falling asleep.

The EEG and FEMG signals obtained from the patient in the way as described above can very advantageously be processed to monitor the state of consciousness by using State Entropy parameters, ie. State Entropy (SE) and Response Entropy (RE). State Entropy corresponds to entropy of the EEG signal and Response Entropy corresponds to entropy of the EEG and FEMG. The idea of RE and SE indices can be seen in FIG. 3. The FEMG signal, ie. RE in FIG. 3, is dominating when the patient is awake and ceases when the patient falls asleep. Then EEG signal, ie. SE in FIG. 3, becomes dominant and the indices RE and SE have the same values. During an operation there can also emerge certain periods when the RE rises. These situations can be due to inadequate analgesia, noise or artefacts in the signal. So both of the measuring sites are needed to optimize RE and SE information. The electrode configuration shown in FIG. 2 can also be used to record CNS activity of both frontal lobes at the same time.

Figure 4:
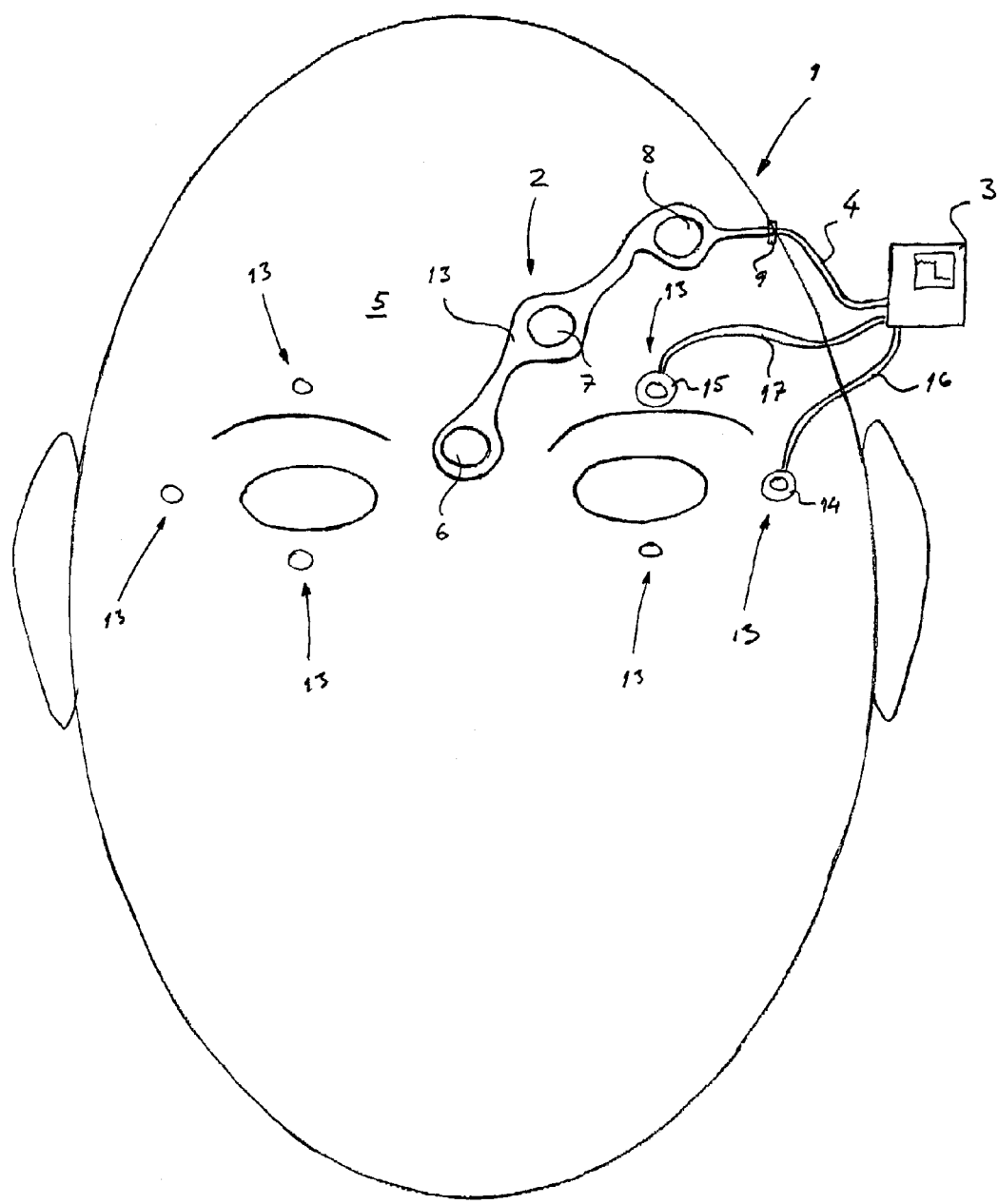
FIG. 4 shows a frontal view of a human head with alternative positions of additional electrodes and FIG. 5 is a plan view of the electrode array of the system shown in FIGS. 1, 2 and 4.

It is also possible to use one or more additional electrodes together with the electrode array described above. Said additional electrodes can be positioned on the area surrounding an eye of the patient in order to record the movements of the eye and to eliminate disturbances caused by said movements. The additional electrodes can be positioned above or/and under the eye or/and adjacent to the eye as shown by reference numeral 13 in FIG. 4. In the embodiment of FIG. 4 two additional electrodes 14, 15 are used. The additional electrodes are connected by using cables 16, 17 to the monitor 3. It is also possible to connect the additional electrodes to the monitor via connector 9 by designing the connector to have some additional inputs. In this connection it must be noted that FIG. 4 shows only one eventual embodiment, it is quite possible also to position the additional electrodes above and under the eye or under and adjacent to the eye etc. It is further possible to use only one additional electrode positioned on one of the positions 13, but better results can be achieved by using two additional electrodes.

The embodiments described above are by no means intended to limit the invention, but the invention may be modified completely freely within the scope of the claims. Thus it is obvious that the details need not be exactly identical with those shown in the Figures and described in the text, but other solutions are also possible. For example the positions of the electrodes shown in Figures are not the only possible positions, but it is quite possible within the spirit of the invention to use also slightly different positions etc.

The invention claimed is:

1. Method of positioning electrodes in an electrode array consisting of three electrodes for central nervous system (CNS) monitoring from the forehead of a patient's head, said method comprising the steps of:
    positioning a first electrode of said three electrodes between the eyebrows or above the eyebrows near frontalis and orbicularis muscles of the patient;
    positioning a third electrode of said three electrodes apart from the first electrode on the hairless fronto-lateral area of the frontal lobe of the patient; and
    positioning a second electrode between the first and the third electrodes on the forehead of the patient.

2. The method of claim 1, in which the first and the third electrodes are measuring electrodes and the second electrode is a ground electrode.

3. The method of claim 2, in which the second electrode is positioned essentially in the middle of the first and the third electrodes having essentially the same distance to said first and third electrodes.

4. The method of claim 2, in which the positioning of the first and the third electrodes enables the first and third electrodes to obtain electroencephalography (BEG) signals.

5. The method of claim 4 in which the positioning of the first electrode enables the first electrode to obtain mainly frontal electromyography (FEMG) signals when the patient is awake or the patient feels pain.

6. The method of claim 4 in which the positioning of the third electrode enables the third electrode to obtain mainly electroencephalography (EEG) signals from the fronto-lateral area of the forehead.

7. The method of claim 1, in which the second electrode is positioned essentially in the middle of the first and the third electrodes having essentially the same distance to said first and third electrodes.

8. The method of claim 7, in which the positioning of the first and the third electrodes enables the first and third electrodes to obtain electroencephalography (EEG) signals.

9. The method of claim 8 in which the positioning of the first electrode enables the first electrode to obtain mainly frontal electromyography (FEMG) signals when the patient is awake or the patient feels pain.

10. The method of claim 8 in which the positioning of the third electrode enables the third electrode to obtain mainly electroencephalography (EEG) signals from the fronto-lateral area of the forehead.

11. The method of claim 1, in which the positioning of the first and the third electrodes enables the first and third electrodes to obtain electroencephalography (EEG) signals.

12. The method of claim 11, in which the positioning of the first electrode enables the first electrode to obtain mainly frontal electromyography (FEMG) signals when the patient is awake or the patient feels pain.

13. The method of claim 11, in which the positioning of the third electrode enables the third electrode to obtain mainly electroencephalography (EEG) signals from the fronto-lateral area of the forehead.

14. The method of claim 1, further comprising the step of positioning at least one additional electrode separate from said three electrode array on the area surrounding the eye of the patient to monitor the movements of the eye.

15. The method of claim 14, in which two additional electrodes are used.

16. The method of claim 15, in which the additional electrodes are positioned above or/and under the eye or/and adjacent to the eye.

17. The method of claim 14, in which the additional electrodes are positioned above or/and under the eye or/and adjacent to the eye.

* * * * *